United States Patent [19]

Phanstiel et al.

[11] Patent Number: 5,159,075
[45] Date of Patent: Oct. 27, 1992

[54] SUBSTITUTED CHLOROTRIAZINES USEFUL FOR REACTIVE CAPPING OF POLYPHENYLENE ETHERS

[75] Inventors: Otto Phanstiel, Clifton Park; Sterling B. Brown, Schenectady, both of N.Y.

[73] Assignee: General Electric Company, Schenectady, N.Y.

[21] Appl. No.: 654,444

[22] Filed: Feb. 11, 1991

Related U.S. Application Data

[63] Continuation-in-part of Ser. No. 534,622, Jun. 7, 1990, abandoned.

[51] Int. Cl.$^5$ ............................................. C07D 251/12
[52] U.S. Cl. ...................................... 544/218; 544/214
[58] Field of Search ................................. 544/218, 214

[56] References Cited

U.S. PATENT DOCUMENTS 4,407,748 12/1989 Gorbacheva .
4,895,945 1/1990 Brown et al. ...................... 544/218

Primary Examiner—Marianne Cintins
Assistant Examiner—John Peabody
Attorney, Agent, or Firm—William H. Pittman; James C. Davis, Jr.

[57] ABSTRACT

Substituted alkoxy- or alkylthiochlorotriazines wherein the substituents on the alkoxy groups are chlorine, bromine or dialkylphosphato are useful as capping agents for polyphenylene ethers. The capped polyphenylene ethers form copolymers with other polymers containing nucleophilic groups, including polyesters, polyamides and functionalized olefin polymers. Such copolymers serve as compatibilizers in the formation of blends having high impact strength.

20 Claims, No Drawings

SUBSTITUTED CHLOROTRIAZINES USEFUL FOR REACTIVE CAPPING OF POLYPHENYLENE ETHERS

This application is a continuation-in-part of copending application Serial No. 07/534,622, now abandoned.

This invention relates to the preparation of reactive triazine-capped polyphenylene ethers, and more particularly to reagents useful therefor.

The polyphenylene ethers are a widely used class of thermoplastic engineering resins characterized by excellent hydrolytic stability, dimensional stability, toughness, heat resistance and dielectric properties. However, they are deficient in certain other properties such as workability and solvent resistance. Therefore, there is a continuing search for means for modifying polyphenylene ethers to improve these other properties.

Among the means being studied are blending of polyphenylene ethers with certain other resinous materials such as polyesters, polyamides or olefin polymers. Blends of these other materials with polyphenylene ethers are, however, usually incompatible. Molded parts fabricated from such blends are generally brittle and may undergo catastrophic delamination upon impact.

Compatibilization of blends of polyphenylene ethers with these other polymers may be achieved by several methods. A frequently preferred method is the formation of a copolymer of the polyphenylene ether with the other polymer; when present in the blend, said copolymer serves as a compatibilizer for the uncopolymerized constituents.

One method for preparing copolymers of polyphenylene ethers with polyesters, polyamides and the like is disclosed in copending, commonly owned application Serial No. 07/351,905. This method comprises capping the polyphenylene ether by reaction with an epoxychlorotriazine such as 2-chloro-4,6-diglycidoxy-1,3,5-triazine, 2-chloro-4-(n-butoxy)-6-glycidoxy-1,3,5-triazine or 2-chloro-4-(2,4,6-trimethylphenoxy)-6-glycidoxy-1,3,5-triazine. Such capped polyphenylene ethers readily form copolymers with nucleophilic polymers such as polyesters, polyamides and functionalized olefin polymers, and blends containing such copolymers have numerous desirable properties including high impact and tensile strengths and structural integrity.

However, the use of epoxychlorotriazines as capping agents has certain disadvantages. Among these are the necessity to use compounds such as glycidol in the preparation of the epoxychlorotriazines. Glycidol is expensive, and also has carcinogenic properties. Interest continues, therefore, in the development of new capping reagents capable of forming polyphenylene ethers which are reactive with other polymers. The present invention includes a class of such capping reagents.

The invention includes substituted alkoxy- or alkylthiochlorotriazines having the formula

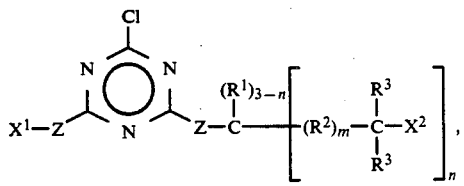

wherein:
$X^1$ is an alkyl, cycloalkyl or aromatic radical or

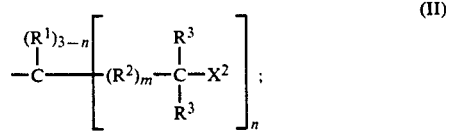

$X^2$ is a group displaceable by nucleophilic aliphatic substitution;
each $Z$ is independently oxygen or sulfur;
each $R^1$ is independently hydrogen, $C_{1-4}$ primary or secondary alkyl or a non-hydrocarbon substituent substantially inert to displacement by nucleophilic moieties;
$R^2$ is a $C_{1-3}$ alkylene radical which is unsubstituted or is substituted with moieties selected from the group consisting of $C_{1-4}$ primary or secondary alkyl radicals and non-hydrocarbon substituents as defined for $R^1$;
each $R^3$ is independently $R1$ or $X^2$;
$m$ is 0 or 1; and
$n$ is 1-3.

It is apparent from formula I that the chlorotriazines of this invention are characterized by the presence of a single chlorine atom on the triazine ring, said chlorine atom being reactive with the terminal hydroxy group on a polyphenylene ether to effect capping thereof. Also present on the triazine ring is a $ZX^1$ moiety, wherein $Z$ is oxygen or sulfur, usually oxygen, and $X^1$ may be an alkyl or cycloalkyl radical, typically lower alkyl (i.e., alkyl of up to 7 carbon atoms) and especially primary or secondary lower alkyl; an aromatic radical, typically monocyclic and containing 6–10 carbon atoms and especially an aromatic hydrocarbon radical; or a radical of formula II. The aromatic radicals are often preferred by reason of the availability of reagents which provide them; the 2,6-xylyl and mesityl (2,4,6-trimethylphenyl) radicals are often particularly preferred.

The $X^2$ radical may be any group capable of displacement by nucleophilic aliphatic substitution. Examples of such groups are chlorine, bromine, iodine, alkylsulfonate, arylsulfonate, carboxylate, phosphate, phosphonate, phosphinate, thiophosphate, thiophosphonate and thiophosphinate groups. Preferred displaceable radicals include chlorine, bromine and

wherein $Z$ is as previously defined and each $R^4$ is a $C_{1-30}$ primary or secondary alkyl, cycloalkyl, aromatic or alkaryl radical or both $R^4$ radicals together with the P and Z atoms form a cyclic structure. Most often, each $Z$ is oxygen and each $R^4$ is a $C_{1-8}$ primary alkyl radical, especially methyl, ethyl or n-butyl. The n-butyl compounds are frequently especially preferred by reason of the ease of preparation of the reagent 2-hydroxyethyl di-n-butyl phosphate, used in their synthesis; said reagent is relatively water-insoluble and can be prepared from ethylene glycol and di-n-butyl phosphite without the need for laborious back-extractions after removal of unreacted ethylene glycol by water washing.

The $R^1$ radicals may be hydrogen or $C_{1-4}$ primary or secondary alkyl. When alkyl, they are preferably methyl or ethyl. They may also be non-hydrocarbon substituents which are not displaced under the conditions encountered during capping of a polyphenylene ether and reaction of the capped polyphenylene ether with another polymer containing nucleophilic groups. Illustrative substituents of this type are acyl, nitro, alkylsulfoxy and alkylsulfone. Most preferably, each $R^1$ is hydrogen.

There may also be present an $R^2$ group (when m is 1) which is a $C_{1-3}$ alkylene radical. It may be unsubstituted or substituted with moieties of the type described hereinabove with reference to $R^1$. When present, it is most often unsubstituted; i.e., it is a methylene, ethylene or trimethylene radical. However, the preferred alkoxychlorotriazines are those in which m is 0; i.e., those which do not contain an $R^2$ radical.

The $R^3$ values may be hydrogen, $R^1$ or $X^2$ as described hereinabove. They are most often hydrogen or $X^2$, and preferably hydrogen.

The carbon atom in formula I which is linked by oxygen or sulfur to the triazine ring contains from 0 to 2 $R^1$ radicals attached thereto, with the remainder of its valence bonds being satisfied by the bracketed moieties. Most often, n is 1; that is, only one such bracketed moiety is present.

The substituted chlorotriazines of this invention may be prepared by the reaction of cyanuric chloride (i.e., 2,4,6-trichlorotriazine) with a first hydroxy or thio compound of the formula

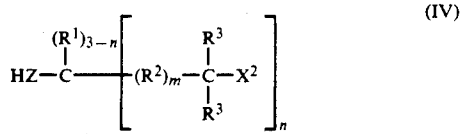

(IV)

wherein R1-3, $X^{1-2}$, Z, m and n are as previously defined, and preferably also sequentially with a second hydroxy or thio compound of the formula $X^1ZH$. The order in which reaction with the two hydroxy or thio compounds takes place is not critical.

In the first of the sequential reactions, the ratio of equivalents of the first hydroxy or thio compound to cyanuric chloride is in the range of about 0.5-1.5:1. It is preferably about 0.99-1.01:1, since the use of lesser amounts of hydroxy or thio compound will result in low yields and the use of greater amounts will cause displacement of more than one of the chlorine atoms on the cyanuric chloride. The intermediate product desired, and formed in predominant amount, in this reaction is a monosubstituted dichlorotriazine.

In the second reaction, the monosubstituted dichlorotriazine undergoes further reaction with the second hydroxy or thio compound. Ratios of equivalents of said second hydroxy or thio compound to monosubstituted dichlorotriazine in this reaction are in the same general and preferred ranges as for the first reaction. (For the purposes of this invention, the equivalent weights of cyanuric chloride, monosubstituted dichlorotriazine and hydroxy or thio compound are respectively one-third, half and the same as their molecular weights.) This may mean the use in the second reaction of a quantity of the second hydroxy or thio compound less than the stoichiometric amount based on cyanuric chloride originally employed, since the yield in the first reaction is frequently less than 100% and it is usually preferred to wash with water to remove water-soluble salts formed as by-products; such washing will inherently result in hydrolysis of a small proportion of the chlorotriazines present.

These reactions are usually most efficiently conducted at temperatures below about 10° C., typically between about −10° and 10° C., in the presence of a suitable hydrogen chloride scavenger such as an alkali metal hydroxide. It is frequently preferred to employ a relatively non-polar solvent such as chloroform, methylene chloride, toluene, xylene or chlorobenzene. It is also frequently advantageous to employ a phase transfer catalyst. Any of such catalysts which are stable and effective under the prevailing reaction conditions may be used; those skilled in the art will readily perceive which ones are suitable. Particularly preferred are the tetraalkylammonium chlorides wherein at least two alkyl groups per molecule, typically 2 or 3, contain about 5-20 carbon atoms.

Following completion of the sequential reactions, the substituted chlorotriazine may be isolated by conventional methods. These typically include washing with water as previously described to remove inorganic salts, stripping of solvent and (where appropriate) recrystallization.

The preparation of the substituted chlorotriazines of this invention is illustrated by the following examples.

EXAMPLE 1

A 3-necked 500-ml. round-bottomed flask equipped with a magnetic stirrer, a pressure-equalized addition funnel and a thermometer was charged with 21.81 grams (118 mmol.) of cyanuric chloride, 10 grams (124.2 mmol.) of 2-chloroethanol and 200 ml. of methylene chloride. The mixture was cooled to 0° C., there was added 4 drops of a commercially available methyltrialkylammonium chloride in which the alkyl groups contained 8-10 carbon atoms, and 11.92 grams (149 mmol.) of 50% aqueous sodium hydroxide solution was added dropwise, with stirring, whereupon an exothermic reaction took place and cooling was continued to maintain a temperature no higher than 5° C. The mixture was warmed to room temperature and stirred for 4 hours, after which 16.91 grams (124 mmol.) of mesitol was added and the flask was again cooled to 0° C. An additional 9.96 grams (125 mmol.) of sodium hydroxide solution was added under the same conditions, and the mixture was warmed to room temperature and stirred overnight.

The aqueous and organic phases were separated and the organic phase was washed three times with distilled water, dried over anhydrous magnesium sulfate, filtered and vacuum stripped. There was obtained 34.3 grams (88% of theoretical) of the desired 2-chloro-4-(2-chloroethoxy)-6-(2,4,6-trimethylphenoxy)-1,3,5-triazine. The structure of the product was confirmed by proton nuclear magnetic resonance spectroscopy.

EXAMPLE 2

The procedure of Example 1 was repeated, except that the order of addition of mesitol and 2-chloroethanol was reversed. The same product was obtained.

EXAMPLE 3

The procedure of Example 1 was repeated, substituting 2-bromoethanol on an equimolar basis for the 2-chloroethanol. The product was the desired 2-chloro-4-(2-bromoethoxy)-6-(2,4,6-trimethylphenoxy)-1,3,5-triazine.

EXAMPLE 4

A 3-necked 1-liter round-bottomed flask equipped with a magnetic stir bar, 50-ml. pressure-equalized addition funnel and thermometer was charged with 31.45 grams (171 mmol.) of cyanuric chloride, 33.8 grams (171 mmol.) of 2-hydroxyethyl diethyl phosphate and 350 ml. of methylene chloride. The mixture was stirred for 5 minutes until homogeneous, whereupon there was added 4 drops of the tetraalkylammonium chloride employed in Example 1. The flask was cooled to 0° C. and 17.06 grams (213 mmol.) of 50% aqueous sodium hydroxide solution was added over 15 minutes, while the temperature was maintained below 6° C. The addition funnel was flushed with 3 ml. of deionized water and the mixture was stirred for 5 minutes at 5° C. and then allowed to warm to room temperature and stirred overnight. There was then added 18.1 grams (133 mmol.) of mesitol, and the mixture was again maintained in the range of 0°–5° C. as 12.77 grams (160 mmol.) of sodium hydroxide solution was added.

The mixture was warmed to room temperature and stirred for 30 minutes. The organic layer was removed, washed three times with 10% aqueous sodium hydroxide solution and three times with deionized water, and dried over magnesium sulfate. After filtration, the solvent was vacuum stripped to yield 54 grams of a white oil which was shown by proton nuclear magnetic resonance spectroscopy to comprise the desired 2-chloro-4-(2-diethylphosphatoethoxy)-6-(2,4,6-trimethylphenoxy)-1,3,5-triazine. There was also present as an impurity, in the amount of 16%, 2-chloro-4,6-bis(2,4,6-trimethylphenoxy)-1,3,5-triazine.

EXAMPLE 5

A solution of 10.93 kg. (89.49 equivalents) of 2,6-xylenol in 90.7 liters of toluene was cooled to 5 C and there were added 16.34 kg. (265.8 equivalents) of cyanuric chloride and 440 grams of the tetraalkylammonium chloride of Example 1. The mixture was stirred and 7.44 kg. of 50% aqueous sodium hydroxide solution (93.03 equivalents) was added at a rate to maintain the temperature below 5° C. When sodium hydroxide addition was complete, the mixture was allowed to warm to room temperature over 30 minutes and was analyzed by high pressure liquid chromatography, which showed that less than 1% of the cyanuric chloride and 2,6-xylenol originally introduced remained in the mixture. Deionized water, 84.8 liters, was added with stirring, the mixture was allowed to separate into two layers and the aqueous layer was removed and discarded.

The organic layer was cooled to 10° C. and 27.32 kg. of 83% pure 2-hydroxyethyl di-n-butyl phosphate (89.49 equivalents) was added. Stirring was continued as 7.80 kg. (97.46 equivalents) of 50% sodium hydroxide solution was added at a rate to maintain the temperature below 5° C. The mixture was allowed to warm to room temperature over 1 hour, whereupon analysis showed the presence of less than 1% of the original amount of the intermediate 2,6-dimethylphenyl dichlorocyanurate. Deionized water, 84.8 liters, was again added and the mixture was stirred and allowed to settle. The aqueous layer was removed and discarded, and the organic layer was further washed until the washings had a pH of 7. The organic solution was then distilled under reduced pressure until all the remaining water had been removed as a toluene-water azeotrope, and the residue was cooled. It was shown by high pressure liquid chromatographic analysis to be a toluene solution of the desired 2-chloro-4-(2-di-n-butylphosphatoethoxy)-6-(2,6-xylenoxy)-1,3,5-triazine.

EXAMPLE 6

The procedure of Example 5 was repeated, except that 10.93 kg. (89.49 equivalents) of 2,6-xylenol and 7.44 kg. (93.03 equivalents) of sodium hydroxide solution were employed in the first reaction, and 24.6 kg. of 83% pure 2-hydroxyethyl di-n-butyl phosphate (80.4 equivalents) in the second reaction. The desired product was obtained in 90.4% yield.

The substituted chlorotriazines of this invention are useful as reactive capping agents for polyphenylene ethers. The resulting capped polyphenylene ethers and the method for their preparation are claimed in copending, commonly owned application Ser. No. 07/787,152.

The polyphenylene ethers which may be capped encompass numerous variations and modifications all of which are applicable to the present invention, including but not limited to those described hereinafter.

The polyphenylene ethers comprise a plurality of structural units having the formula

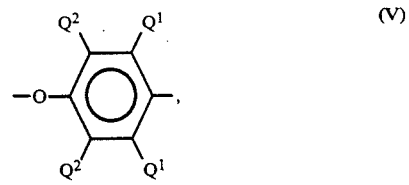

(V)

wherein each $Q^1$ is independently halogen, primary or secondary lower alkyl, phenyl, haloalkyl, aminoalkyl, hydrocarbonoxy, or halohydrocarbonoxy wherein two or more carbon atoms separate the halogen and oxygen atoms; and each $Q^2$ is independently hydrogen, halogen, primary or secondary lower alkyl, phenyl, haloalkyl, hydrocarbonoxy or halohydrocarbonoxy as defined for $Q^1$. Examples of primary lower alkyl groups suitable as $Q^1$ and $Q^2$ are methyl, ethyl, n-propyl, n-butyl, isobutyl, n-amyl, isoamyl, 2-methylbutyl, n-hexyl, 2,3-dimethylbutyl, 2-, 3- or 4-methylpentyl and the corresponding heptyl groups. Examples of secondary lower alkyl groups are isopropyl, sec-butyl and 3-pentyl. Preferably, any alkyl radicals are straight chain rather than branched. Most often, each $Q^1$ is alkyl or phenyl, especially $C_{1-4}$ alkyl, and each $Q^2$ is hydrogen. Suitable polyphenylene ethers are disclosed in a large number of patents.

Both homopolymer and copolymer polyphenylene ethers are included. Suitable homopolymers are those containing, for example, 2,6-dimethyl-1,4-phenylene ether units. Suitable copolymers include random copolymers containing such units in combination with (for example) 2,3,6-trimethyl-1,4-phenylene ether units. Many suitable random copolymers, as well as homopolymers, are disclosed in the patent literature.

Also included are polyphenylene ethers containing moieties which modify properties such as molecular weight, melt viscosity and/or impact strength. Such polymers are described in the patent literature and may be prepared by grafting onto the polyphenylene ether in known manner such vinyl monomers as acrylonitrile and vinylaromatic compounds (e.g., styrene), or such polymers as polystyrenes and elastomers. The product typically contains both grafted and ungrafted moieties. Other suitable polymers are the coupled polyphenylene ethers in which the coupling agent is reacted in known manner with the hydroxy groups of two polyphenylene ether chains to produce a higher molecular weight polymer containing the reaction product of the hydroxy groups and the coupling agent, provided substantial proportions of free hydroxy groups remain present. Illustrative coupling agents are low molecular weight polycarbonates, quinones, heterocycles and formals.

The polyphenylene ether generally has a number average molecular weight within the range of about 3,000–40,000 and a weight average molecular weight within the range of about 20,000–80,000, as determined by gel permeation chromatography. Its intrinsic viscosity is most often in the range of about 0.15–0.6 dl./g., as measured in chloroform at 25° C.

The polyphenylene ethers are typically prepared by the oxidative coupling of at least one corresponding monohydroxyaromatic compound. Particularly useful and readily available monohydroxyaromatic compounds are 2,6-xylenol (wherein each $Q^1$ is methyl and each $Q^2$ is hydrogen), whereupon the polymer may be characterized as a poly(2,6-dimethyl-1,4-phenylene ether), and 2,3,6-trimethylphenol (wherein each $Q^1$ and one $Q^2$ is methyl and the other $Q^2$ is hydrogen).

A variety of catalyst systems are known for the preparation of polyphenylene ethers by oxidative coupling. There is no particular limitation as to catalyst choice and any of the known catalysts can be used. For the most part, they contain at least one heavy metal compound such as a copper, manganese or cobalt compound, usually in combination with various other materials.

A first class of preferred catalyst systems consists of those containing a copper compound. Such catalysts are disclosed, for example, in U.S. Pat. Nos. 3,306,874, 3,306,875, 3,914,266 and 4,028,341. They are usually combinations of cuprous or cupric ions, halide (i.e., chloride, bromide or iodide) ions and at least one amine.

Catalyst systems containing manganese compounds constitute a second preferred class. They are generally alkaline systems in which divalent manganese is combined with such anions as halide, alkoxide or phenoxide. Most often, the manganese is present as a complex with one or more complexing and/or chelating agents such as dialkylamines, alkanolamines, alkylenediamines, o-hydroxyaromatic aldehydes, o-hydroxyazo compounds, ω-hydroxyoximes (monomeric and polymeric), o-hydroxyaryl oximes and β-diketones. Also useful are known cobalt-containing catalyst systems. Suitable manganese and cobalt-containing catalyst systems for polyphenylene ether preparation are known in the art by reason of disclosure in numerous patents and publications.

The polyphenylene ethers which may be employed for the purposes of this invention include those which comprise molecules having at least one of the end groups of the formulas

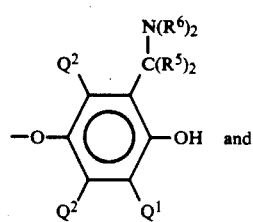

(VI)

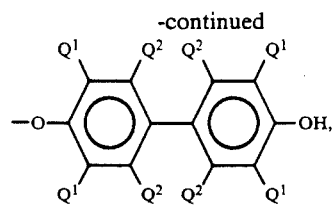

(VII)

wherein $Q^1$ and $Q^2$ are as previously defined; each $R^5$ is independently hydrogen or alkyl, with the proviso that the total number of carbon atoms in both $R^5$ radicals is 6 or less; and each $R^6$ is independently hydrogen or a $C_{1-6}$ primary alkyl radical. Preferably, each $R^5$ is hydrogen and each $R^6$ is alkyl, especially methyl or n-butyl.

Polymers containing the aminoalkyl-substituted end groups of formula VI are typically obtained by incorporating an appropriate primary or secondary monoamine as one of the constituents of the oxidative coupling reaction mixture, especially when a copper- or manganese-containing catalyst is used. Such amines, especially the dialkylamines and preferably di-n-butylamine and dimethylamine, frequently become chemically bound to the polyphenylene ether, most often by replacing one of the α-hydrogen atoms on one or more $Q^1$ radicals. The principal site of reaction is the $Q^1$ radical adjacent to the hydroxy group on the terminal unit of the polymer chain. During further processing and/or blending, the aminoalkyl-substituted end groups may undergo various reactions, probably involving a quinone methide-type intermediate of the formula

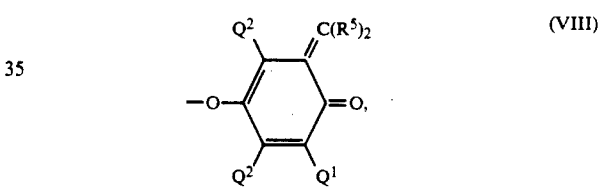

(VIII)

with numerous beneficial effects often including an increase in impact strength and compatibilization with other blend components. Reference is made to U.S. Pat. Nos. 4,054,553, 4,092,294, 4,477,649, 4,477,651 and 4,517,341, the disclosures of which are incorporated by reference herein.

Polymers with 4-hydroxybiphenyl end groups of formula VII are often especially useful in the present invention. They are typically obtained from reaction mixtures in which a by-product diphenoquinone of the formula

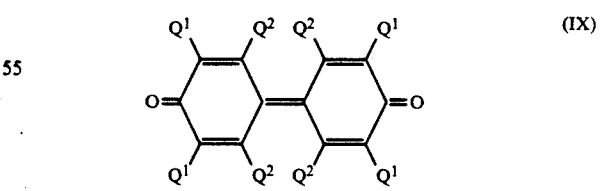

(IX)

is present, especially in a copper-halide-secondary or tertiary amine system. In this regard, the disclosure of U.S. Pat. No. 4,477,649 is again pertinent as are those of U.S. Pat. Nos. 4,234,706 and 4,482,697, which are also incorporated by reference herein. In mixtures of this type, the diphenoquinone is ultimately incorporated into the polymer in substantial proportions, largely as an end group.

In many polyphenylene ethers obtained under the above-described conditions, a substantial proportion of the polymer molecules, typically constituting as much as about 90% by weight of the polymer, contain end groups having one or frequently both of formulas VI and VII. It should be understood, however, that other end groups may be present and that the invention in its broadest sense may not be dependent on the molecular structures of the polyphenylene ether end groups. It is, however, required that a substantial proportion of free, non-hydrogen bonded hydroxy groups be present; that is, that a substantial proportion of hydroxy-terminated end groups have structures other than that of formula VI.

The use of polyphenylene ethers containing substantial amounts of unneutralized amino nitrogen may afford compositions with undesirably low impact strengths. The amino compounds include, in addition to the aforementioned aminoalkyl end groups, traces of amine (particularly secondary amine) from the catalyst used to form the polyphenylene ether.

The present invention therefore includes the use of polyphenylene ethers in which a substantial proportion of amino compounds has been removed or inactivated. Polymers so treated contain unneutralized amino nitrogen, if any, in amounts no greater than 800 ppm. and more preferably in the range of about 100-800 ppm.

A preferred method of inactivation is by extrusion of the polyphenylene ether at a temperature within the range of about 230°-350° C., with vacuum venting. This is preferably achieved in a preliminary extrusion step, by connecting the vent of the extruder to a vacuum pump capable of reducing the pressure to about 200 torr or less.

It is believed that this inactivation method aids in the removal by evaporation of any traces of free amines (predominantly secondary amines) in the polymer, including amines generated by conversion of aminoalkyl end groups to quinone methides of the type represented by formula VIII.

It will be apparent to those skilled in the art from the foregoing that the polyphenylene ethers contemplated for use in the present invention include all those presently known, irrespective of variations in structural units or ancillary chemical features.

The reaction between the substituted chlorotriazine and the polyphenylene ether is conducted in the presence of an alkaline reagent which serves as a catalyst and/or hydrogen chloride acceptor. Various types of alkaline reagents may be employed; they include alkali metal hydroxides, most often sodium hydroxide or potassium hydroxide, and amines, most often tertiary amines such as pyridine. When amines are used, the reaction may take place in a homogeneous organic medium, typically provided by a non-polar organic liquid such as toluene, xylene or chlorobenzene.

It is generally preferred to employ an alkali metal hydroxide as the base, ordinarily in the form of an aqueous solution and in combination with the same types of non-polar organic liquids as reaction media. The reaction is then heterogeneous and it is preferred to incorporate in the mixture a phase transfer catalyst of the type previously described. Reaction temperatures in such heterogeneous media are typically in the range of about 20°-100° C.

The proportions of substituted chlorotriazine and polyphenylene ether may be varied widely, depending upon the proportion of copolymer desired in the blend to be compatibilized. Molar ratios of substituted chlorotriazine to polyphenylene ether, the latter in terms of non-hydrogen bonded hydroxy end groups, are typically in the range of about 0.1-2.0:1. The molar ratio of base to polyphenylene ether is usually in the range of about 1-2:1, and the phase transfer catalyst (when employed) is present in a minor amount effective to catalyze the reaction, usually about 0.1-2.0% (by weight) and preferably about 0.5-1.0% based on polyphen,ylene ether.

It is within the scope of the invention to employ a reactive extrusion process to prepare the capped polyphenylene ether. This may involve, for example, separate feeding of chlorotriazine and polyphenylene ether, at least one being in solution, to an extruder, followed by removal of the solvent by volatilization or addition of an anti-solvent and isolation of a slurry as the extrudate.

Following completion of the capping reaction, organic solvent can be removed by conventional operations, typically including precipitation with a non-solvent. Among the non-solvents which may be employed are methanol, 1-propanol, acetone, acetonitrile and mixtures thereof.

The molecular structure of the end groups of the substituted chlorotriazine-capped polyphenylene ethers is believed to correspond to the formula

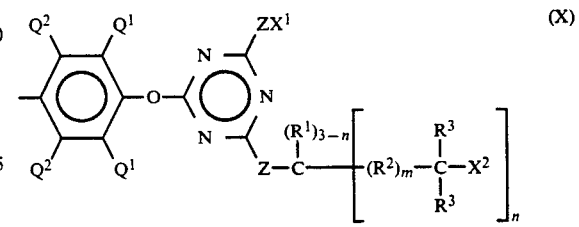

wherein $Q^{1-2}$, $R^{1-3}$, $X^{1-2}$, Z, m and n are as previously defined.

It should be noted that the "end groups" in polyphenylene ethers having 4-hydroxybiphenyl end groups of formula VII may be defined in two senses: in terms of formula VII as incorporating said 4-hydroxybiphenyl moiety, and in terms of only the hydroxy-substituted aromatic ring in that moiety. Formula X employs the term in its second sense.

The preparation of capped polyphenylene ethers from the substituted chlorotriazines of this invention is illustrated by the following examples. In each example, the polyphenylene ether employed was a commercially available poly(2,6-dimethyl-1,4-phenylene ether) having an intrinsic viscosity in chloroform at 25° C. of 0.40 dl./g. Molar proportions of polyphenylene ether are in terms of non-hydrogen bonded hydroxy end groups.

EXAMPLE 7

A 3-necked 12-liter flask equipped with a mechanical stirrer, a thermometer and a nitrogen purge system was charged with 3.7 liters of toluene and 800 grams (47 mmol.) of polyphenylene ether. The mixture was heated to 55° C. until the polyphenylene ether had dissolved, whereupon 4 grams of the phase transfer catalyst solution of Example 1 and 5.65 grams (71 mmol.) of 50% aqueous sodium hydroxide solution were added. The mixture was vigorously stirred at 55° C. for 15 minutes, after which 34.3 grams (104 mmol.) of the product of Example 1 was added and stirring was continued for 35 minutes. The remaining base was quenched by bubbling gaseous carbon dioxide through the mixture for 7 minutes, and the product was isolated by pouring into methanol, filtration and drying in a vacuum oven. There was obtained 806 grams of the desired capped polyphenylene ether; its molecular structure was confirmed by proton nuclear magnetic resonance spectroscopy.

EXAMPLE 8

The procedure of Example 7 was repeated, substituting 94 mmol. of the product of Example 3 for that of Example 1. There was obtained 802 grams of the desired capped polyphenylene ether.

EXAMPLE 9

The procedure of Example 7 was repeated, substituting 41.96 grams (94 mmol.) of the product of Example 4 for that of Example 1. There was obtained 802 grams of the desired capped polyphenylene ether.

Polyphenylene ethers capped with the substituted chlorotriazines of this invention react with other polymers containing reactive groups, particularly those capable of nucleophilic aliphatic addition or substitution such as amine, hydroxy, thio and carboxy groups and functional derivatives of said carboxy groups, including ester and anhydride moieties, to form copolymer-containing compositions. Such compositions are disclosed and claimed in copending, commonly owned application Ser. No. 07/654,443.

Said reactive groups may be present at any location in the other polymer molecule; i.e., they may be end groups, substituents and grafted moieties. Thus, it is possible to form copolymer-containing compositions from numerous polymers which are otherwise incompatible with polyphenylene ethers, including polyesters, polyamides and carboxy-functionalized olefin polymers. By reason of the presence of the copolymer, such compositions are compatible and may be molded into articles having excellent physical properties. They are also useful for further compatibilizing blends of the two polymers to form molding compositions having similar excellent properties.

It is frequently preferred, particularly when the other polymer is a polyester or polyamide or is otherwise subject to hydrolytic degradation, to employ a capped polyphenylene ether in which $X^2$ is a phosphato group rather than halogen. This is true because of the increased rate of hydrolysis of the other polymer in the presence of by-product hydrogen halides when $X^2$ is chlorine or bromine, which frequently results in the formation of compositions having somewhat lower impact strengths than when $X^2$ is phosphato. Alternatively, a suitable hydrogen halide scavenger may be employed when $X^2$ is halogen.

Polyesters suitable for preparing copolymer-containing compositions include those comprising structural units of the formula

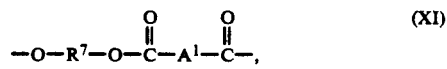

wherein each $R^7$ is independently a divalent aliphatic, alicyclic or aromatic hydrocarbon or polyoxyalkylene radical and $A^1$ is a divalent aromatic radical. Such polyesters include thermoplastic polyesters illustrated by poly(alkylene dicarboxylates), elastomeric polyesters, polyarylates, and polyester copolymers such as copolyestercarbonates. Because the principal reaction which occurs with the substituent groups in the capped polyphenylene ether involves a carboxylic acid group of the polyester, it is highly preferred that said polyester have a relatively high carboxylic end group concentration. Concentrations in the range of about 5–250 microequivalents per gram are generally suitable, with 10–100 microequivalents per gram being preferable, 30–100 being more preferable and 40–80 being particularly desirable.

The polyester may include structural units of the formula

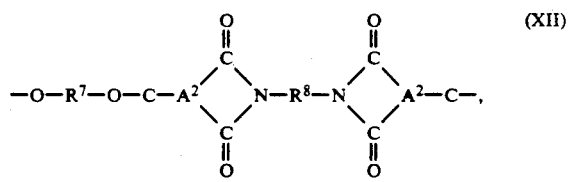

wherein $R^7$ is as previously defined, $R^8$ is a polyoxyalkylene radical and $A^2$ is a trivalent aromatic radical. The $A^1$ radical in formula XI is most often p- or m-phenylene or a mixture thereof, and $A^2$ in formula XII is usually derived from trimellitic acid and has the structure

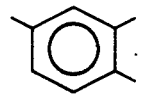

The $R^7$ radical may be, for example, a $C_{2-10}$ alkylene radical, a $C_{6-10}$ aliCyclic radical, a $C_{6-20}$ aromatic radical or a polyoxyalkylene radical in which the alkylene groups contain about 2–6 and most often 4 carbon atoms. As previously noted, this class of polyesters includes the poly(alkylene terephthalates) and the polyarylates. Poly(alkylene terephthalates) are frequently preferred, with poly(ethylene terephthalate) and poly(butylene terephthalate) being most preferred.

The polyester generally has a number average molecular weight in the range of about 20,000–70,000, as determined by intrinsic viscosity (IV) at 30° C. in a mixture of 60% (by weight) phenol and 40% 1,1,2,2-tetrachloroethane.

Polyamides suitable for copolymer formation may be made by any known method. They preferably contain a substantial proportion of amine end groups. In many instances, polyamides in which the amine end group concentration is at least about 60 meq./g. are particularly useful. It is also within the scope of the invention, however, to employ predominantly carboxylic acid-terminated polyamides.

Suitable polyamides include those of the type prepared by the polymerization of a monoamino-monocarboxylic acid or a lactam thereof having at least 2 carbon atoms between the amino and carboxylic acid group, of substantially equimolar proportions of a diamine which contains at least 2 carbon atoms between the amino groups and a dicarboxylic acid, or of a monoaminocarboxylic acid or a lactam thereof as defined above together with substantially equimolar proportions of a diamine and a dicarboxylic acid. The dicarboxylic acid may be used in the form of a functional derivative thereof, for example, an ester or acid chloride.

Examples of the aforementioned monoamino-monocarboxylic acids or lactams thereof which are useful in preparing the polyamides include those compounds containing from 2 to 16 carbon atoms between the amino and carboxylic acid groups, said carbon atoms forming a ring with the —CO—NH— group in the case of a lactam. As particular examples of aminocarboxylic acids and lactams there may be mentioned ε-aminocaproic acid, butyrolactam, pivalolactam, ε-caprolactam, capryllactam, enantholactam, undecanolactam, dodecanolactam and 3- and 4-aminobenzoic acids.

Diamines suitable for use in the preparation of the polyamides include the straight chain and branched chain alkyl, aryl and alkaryl diamines. Illustrative diamines are trimethylenediamine, tetramethylenediamine, pentamethylenediamine, octamethylenediamine, hexamethylenediamine (which is often preferred), trimethylhexamethylenediamine, m-phenylenediamine and m-xylylenediamine.

Suitable dicarboxylic acids include those which contain an aliphatic or aromatic group containing at least 2 carbon atoms separating the carboxy groups. The aliphatic acids are often preferred; they include sebacic acid, octadecanedioic acid, suberic acid, glutaric acid, pimelic acid and adipic acid.

Both crystalline and amorphous polyamides may be employed, with the crystalline species often being preferred by reason of their solvent resistance. Typical examples of the polyamides or nylons, as these are often called, include, for example, polyamide-6 (polycaprolactam), 66 (polyhexamethylene adipamide), 11, 12, 63, 64, 6/10 and 6/12 as well as polyamides from terephthalic acid and/or isophthalic acid and trimethylhexamethylenediamine; from adipic acid and m-xylylenediamines; from adipic acid, azelaic acid and 2,2-bis(p-aminophenyl)propane or 2,2-bis-(p-aminocyclohexyl)propane and from terephthalic acid and 4,4'-diaminodicyclohexylmethane. Mixtures and/or copolymers of two or more of the foregoing polyamides or prepolymers thereof, respectively, are also within the scope of the present invention. Preferred polyamides are polyamide-6, 66, 11 and 12, most preferably polyamide-66.

The olefin polymers (hereinafter sometimes designated "polyolefins") which may be functionalized for use in the preparation of copolymer-containing compositions are homopolymers and copolymers of known aliphatic olefins including ethylene, propylene, 1-butene, 2-butene, 1-pentene, -pentene, 2-methyl-1-pentene, 3-methyl-1-pentene, 1-octene and 1-dodecene. The $C_{2-6}$ olefins are preferred, with ethylene and propylene being most preferred.

For copolymer formation, it is essential for the polyolefin to have the the aforementioned reactive substituents. They may be incorporated in the polyolefin by employing suitable functional comonomers, such as acrylic acid, maleic anhydride or allylamine, in the formation thereof. They may also be provided by graft polymerization on an already prepared polyolefin, using the same monomers, or by other art-recognized means of functionalization. Any of the commercially available graft-functionalized polyolefins may be used, or suitable polymers may be prepared from commercially available unfunctionalized polyolefins such as low density polyethylene, high density polyethylene and polypropylene. Also useful are copolymers with dienes, particlularly non-conjugated dienes; such copolymers include EPDM's as defined hereinafter.

It is highly preferred to employ a blending method which results in the formation of an intimate blend for the preparation of copolymer-containing compositions. Suitable methods include solution blending, although such procedures are of limited applicability to many polymers (especially polyesters and polyamides) by reason of their insolubility in most common solvents. For this reason and because of the availability of melt blending equipment in commercial polymer processing facilities, melt reaction procedures are generally preferred. Conventional melt blending procedures and equipment may be employed, with extrusion often preferred because of its relative convenience and particular suitability. Typical reaction temperatures are in the range of about 175°-350° C. It is usually preferred to extrude with vacuum venting as described hereinabove with reference to uncapped polyphenylene ether, particularly if vacuum venting was not previously employed in the preparation or processing of said polyphenylene ether.

Those skilled in the art will be familiar with blending methods and apparatus capable of intimately blending resinous constituents, especially by kneading. They are exemplified by disc-pack processors and various types of extrusion equipment. Illustrations of the latter are continuous mixers; single screw kneading extruders; corotating, intermeshing and counterrotating, non-intermeshing twin screw extruders having such features as staggered configuration screws, forward-flighted compounders, cylindrical bushings and left-handed screw elements; and extruders having screws which include at least one and preferably two kneading block elements.

In addition to copolymer, the above-described compositions may also contain unreacted polyphenylene ether. This will include any polyphenylene ether molecules having only hydrogen bonded end groups, as well as other polyphenylene ether which is unfunctionalized as a result of incomplete capping, which is functionalized but fails to react with the other polymer or which is introduced in unfunctionalized form. In any event, molded parts produced from said compositions are generally ductile and have higher impact strengths than those produced from simple blends, which are incompatible and often exhibit brittleness or delamination as previously described.

It is also contemplated to include in the blending step impact modifiers compatible with either or both of the polyphenylene ether and the other polymer.

Impact modifiers for polyphenylene ether compositions are well known in the art. They are most often elastomeric polymers, typically derived from one or more monomers selected from the group consisting of olefins, vinyl aromatic monomers, acrylic and alkylacrylic acids and their ester derivatives as well as conjugated dienes. Especially preferred impact modifiers are the rubbery high-molecular weight materials including natural and synthetic polymeric materials showing elasticity at room temperature. They include both homopolymers and copolymers, including random, block, radial block, graft and core-shell copolymers as well as combinations thereof.

Polyolefins or olefin-based copolymers employable in the invention include low density polyethylene, high density polyethylene, linear low density polyethylene, isotactic polypropylene, poly(1-butene), poly(4-methyl- 1-pentene), propylene-ethylene copolymers and the like. Additional olefin copolymers include copolymers of one or more α-olefins, particularly ethylene, with copolymerizable monomers including, for example, vinyl acetate, acrylic acid and alkylacrylic acids as well as the ester derivatives thereof including, for example, ethyl acrylate, methyl methacrylate and the like. Also suitable are the ionomer resins, which may be wholly or partially neutralized with metal ions.

A particularly useful class of impact modifiers are those derived from the vinyl aromatic monomers. These include AB and ABA type block and radial block copolymers and vinyl aromatic conjugated diene core-shell graft copolymers.

An especially preferred subclass of vinyl aromatic monomer-derived resins is the block copolymers comprising monoalkenyl arene (usually styrene) blocks and conjugated diene (e.g., butadiene or isoprene) or olefin (e.g., ethylene-propylene, ethylene-butylene) blocks and represented as AB and ABA block copolymers. The conjugated diene blocks may be partially or entirely hydrogenated, whereupon the properties are similar to the olefin block copolymers.

Suitable AB type block copolymers are disclosed in, for example, U.S. Pat. Nos. 3,078,254; 3,402,159; 3,297,793; 3,265,765 and 3,594,452 and UK Patent 1,264,741, all incorporated herein by reference. Exemplary of typical species of AB block copolymers are polystyrene-polybutadiene (SBR), polystyrene-polyisoprene and poly(alpha-methylstyrene)-polybutadiene. Such AB block copolymers are available commercially from a number of sources, including Phillips Petroleum under the tradename SOLPRENE.

Additionally, ABA triblock copolymers and processes for their production as well as hydrogenation, if desired, are disclosed in U.S. Pat. Nos. 3,149,182; 3,231,635; 3,462,162; 3,287,333; 3,595,942; 3,694,523 and 3,842,029, all incorporated herein by reference.

Examples of triblock copolymers include polystyrene-polybutadiene-polystyrene (SBS), polystyrene-polyisoprene-polystyrene (SIS), poly(α-methylstyrene)-polybutadiene-poly(α-methylstyrene) and poly(α-methylstyrene)-polyisoprene-poly(α-methylstyrene). Particularly preferred triblock copolymers are available commercially as CARIFLEX ®, KRATON D ® and KRATON G ® from Shell.

Another class of impact modifiers is derived from conjugated dienes. While many copolymers containing conjugated dienes have been discussed above, additional conjugated diene modifier resins include, for example, homopolymers and copolymers of one or more conjugated dienes including, for example, polybutadiene, butadiene-styrene copolymers, isoprene-isobutylene copolymers, chlorobutadiene polymers, butadiene-acrylonitrile copolymers, polyisoprene, and the like. Ethylene-propylene-diene monomer rubbers may also be used. These EPDM's are typified as comprising predominantly ethylene units, a moderate amount of propylene units and up to about 20 mole percent of non-conjugated diene monomer units. Many such EPDM's and processes for the production thereof are disclosed in U.S. Pat. Nos. 2,933,480; 3,000,866; 3,407,158; 3,093,621 and 3,379,701, incorporated herein by reference.

Other suitable impact modifiers are the core-shell type graft copolymers. In general, these have a predominantly conjugated diene rubbery core or a predominantly crosslinked acrylate rubbery core and one or more shells polymerized thereon and derived from monoalkenylarene and/or acrylic monomers alone or, preferably, in combination with other vinyl monomers. Such core-shell copolymers are widely available commercially, for example, from Rohm and Haas Company under the trade names KM-611, KM-653, KM-330, and are described in U.S. Pat. Nos. 3,808,180; 4,034;013; 4,096,202; 4,180,494 and 4,292,233.

Also useful are the core-shell copolymers wherein an interpenetrating network of the resins employed characterizes the interface between the core and shell. Especially preferred in this regard are the ASA type copolymers available from General Electric Company and sold as GELOY ™ resin and described in U.S. Pat. No. 3,944,631.

In addition, there may be employed the above-described polymers and copolymers having copolymerized therewith or grafted thereon monomers having functional groups and/or polar or active groups. Finally, other suitable impact modifiers include Thiokol rubber, polysulfide rubber, polyurethane rubber, polyether rubber (e.g., polypropylene oxide), epichlorohydrin rubber, ethylenepropylene rubber, thermoplastic polyester elastomers and thermoplastic ether-ester elastomers.

There may also be present in the copolymer-containing compositions conventional ingredients such as fillers, flame retardants, pigments, dyes, stabilizers, antistatic agents, crystallization aids, mold release agents and the like, as well as resinous components not previously discussed.

The proportions of polyphenylene ether, other polymer and other resinous materials such as impact modifier (if present) are not critical; they may be widely varied to provide compositions having the desired properties. Most often, the polyphenylene ether is employed in an amount in the range of about 5–95%, preferably about 15–70%, of the composition by weight. Impact modifiers such as diblock or triblock copolymers are usually present in an amount up to about 50 parts per 100 parts of polyphenylene ether.

The preparation of copolymer-containing compositions from capped polyphenylene ethers prepared from the substituted chlorotriazines of this invention is illustrated by the following examples. All parts are by weight.

EXAMPLE 10

A dry blend of 20 parts of the product of Example 9, 70 parts of a commercially available poly(butylene terephthalate) having a number average molecular weight of about 50,000 as determined by gel permeation chromatography, and 10 parts of a commercially available triblock copolymer with polystyrene end blocks having weight average molecular weights of 29,000 and a hydrogenated butadiene midblock having a weight average molecular weight of 116,000 was prepared and extruded with vacuum venting at temperatures in the range of 120°–288° C. The extrudate was the desired copolymer-containing composition; it was pelletized, dried for 4 hours at 120° C. and molded into a test specimen which was tested for notched Izod impact strength (ASTM procedure D256). It was found to have an impact strength of 774 joules/m. For comparison, a control, prepared by an identical procedure using a polyphenylene ether which had been capped with 2-chloro-4-ethoxy-6-(2,4,6-trimethylphenoxy)triazine, was found to have an impact strength of 16 joules/m.

EXAMPLES 11-14

Following the procedure of Example 10, compositions were prepared from a capped polyphenylene ether similar to that of Example 9 except that the molar ratio of chlorotriazine to polyphenylene ether was 1.5:1, uncapped polyphenylene ether (in Examples 12-14), the poly(butylene terephthalate) employed in Example 10 and two different impact modifiers: that of Example 10 (Examples 11-12) and a radial teleblock copolymer comprising 80% polybutadiene midblock and 20% polystyrene end blocks. The proportions and impact strengths are given in Table I, in comparison with a control in which no capped polyphenylene ether was present.

TABLE I

| | Example | | | | |
|---|---|---|---|---|---|
| | 11 | 12 | 13 | 14 | Control |
| Polyphenylene ether, parts: | | | | | |
| Capped | 20 | 10 | 30 | 15 | — |
| Uncapped | — | 10 | — | 15 | 30 |
| Polyester, parts | 70 | 70 | 60 | 60 | 60 |
| Impact modifier, parts: | | | | | |
| Diblock | 10 | 10 | — | — | 10 |
| Radial teleblock | — | — | 10 | 10 | — |
| Izod impact strength, joules/m. | 635 | 545 | 860 | 790 | 48 |

EXAMPLES 15-16

Following the procedure of Example 10, blends were prepared from 49 parts of the capped polyphenylene ethers of Examples 7 and 8, 41 parts of a commercially available polyamide-66 having a high amine end group concentration and 10 parts of the impact modifier of Example 10. The impact strengths are given in Table II, in comparison with a control similar to that of Example 10 except for proportions and substitution of polyamide for polyester.

TABLE II

| | Example | | |
|---|---|---|---|
| | 15 | 16 | Control |
| Polyphenylene ether | Ex. 7 | Ex. 8 | Control |
| Izod impact strength, joules/m. | 299 | 401 | 48 |

EXAMPLE 17

Following the procedure of Example 10, a composition was prepared from 49 parts of the capped polyphenylene ether employed in Example 11-14, 41 parts of the polyamide-66 of Examples 15-16 and 10 parts of the impact modifier of Examples 13-14. It had a notched Izod impact strength of 603 joules/m., as compared to 48 joules/m. for a similar blend prepared from uncapped polyphenylene ether.

What is claimed is:

1. A substituted alkoxy- or alkylthiochlorotriazine having the formula

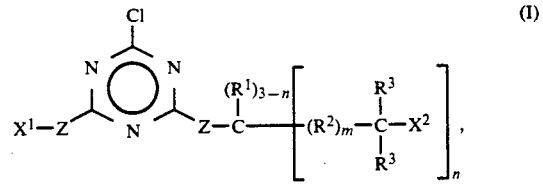

wherein:
$X^1$ is an alkyl, cycloalkyl or aromatic radical or

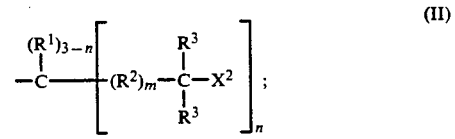

$X^2$ is chlorine, bromine or

wherein each $R^4$ is a $C_{1-30}$ primary or secondary alkyl, aromatic or alkaryl radical or both $R^4$ radicals together with the P and Z atoms form a cyclic structure;
each Z is independently oxygen or sulfur;
each $R^1$ is independently hydrogen or $C_{1-4}$ primary or secondarly alkyl;
$R^2$ is a $C_{1-3}$ alkylene radical which is unsubstituted or is substituted with moieties selected from the group consisting of $C_{1-4}$ primary or secondary alkyl radicals and non-hydrocarbon substituents as defined for $R^1$;
each $R^3$ is independently $R^1$ or $X^2$;
m is 0 or 1; and
n is 1-3.

2. A substitutes chlorotriazine according to claim 1 wherein $X^1$ is an alkyl, cycloalkyl or aromatic radical.

3. A substituted chlorotriazine according to claim 2 wherein m is 0 and n is 1.

4. A substituted chlorotriazine according to claim 3 wherein each Z is oxygen.

5. A substituted chlorotriazine according to claim 4 wherein each $R^3$ is hydrogen.

6. A substituted chlorotriazine according to claim 5 wherein each $R^1$ is hydrogen 7. A substituted chlorotriazine according to claim 6 wherein $X^1$ is a primary or secondary lower alkyl radical.

8. A substituted chlorotriazine according to claim 6 wherein $X^1$ is a monocyclic aromatic radical containing 6-10 carbon atoms.

9. A substituted chlorotriazine according to claim 7 wherein $X^1$ is 2,4,6-trimethylphenyl.

10. A substituted chlorotriazine according to claim 8 wherein $X^1$ is 2,6-xylyl.

11. A substituted chlorotriazine according to claim 6 wherein $X^2$ is chlorine.

12. A substituted chlorotriazine according to claim 6 wherein $X^2$ is bromine.

13. A substituted chlorotriazine according to claim 6 wherein $X^2$ is

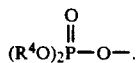

14. A substituted chlorotriazine according to claim 13 wherein $R^4$ is $C_{1-4}$ primary alkyl.

15. A substituted chlorotriazine according to claim 14 wherein $R^4$ is n-butyl.

16. 2-Chloro-4-(2-chloroethoxy)-6-(2,4,6-trimethylphenoxy)-1,3,5-triazine, the compound of formula I wherein $R^1$ and $R^3$ are each hydrogen, $X^1$ is 2,4,6-trimethylphenyl, $X^2$ is chlorine, Z is oxygen, m is 0 and n is 1.

17. 2-Chloro-4-(2-chloroethoxy)-6-(2,4,6-trimethylphenoxy)-1,3,5-triazine.

18. 2-Chloro-4-(2-chloroethoxy)-6-(2,4,6-trimethylphenoxy)-1,3,5-triazine.

19. 2-Chloro-4-(2-chloroethoxy)-6-(2,4,6-trimethylphenoxy)-1,3,5-triazine 20. 2-Chloro-4-(2-chloroethoxy)-6-(2,4,6-trimethylphenoxy)-1,3,5-triazine.

* * * * *